United States Patent
Selmani et al.

(10) Patent No.: US 10,857,176 B2
(45) Date of Patent: Dec. 8, 2020

(54) COMPOSITION COMPRISING POLYGLUCOSAMINE-GLYOXYLATE SOLUTIONS MIXED WITH HYALURONAN

(71) Applicant: OLIGO MEDIC INC., Laval (CA)

(72) Inventors: Amine Selmani, Montréal (CA); Abdellatif Chenite, Kirkland (CA)

(*) Notice: Subject to any disclaimer, the term of this patent is extended or adjusted under 35 U.S.C. 154(b) by 0 days.

(21) Appl. No.: 16/394,125

(22) Filed: Apr. 25, 2019

(65) Prior Publication Data

US 2019/0247421 A1 Aug. 15, 2019

Related U.S. Application Data

(63) Continuation of application No. 15/008,620, filed on Jan. 28, 2016, now abandoned.

(60) Provisional application No. 61/859,921, filed on Jul. 30, 2013.

(51) Int. Cl.
| | | |
|---|---|---|
| A61K 31/722 | (2006.01) | |
| A61K 31/728 | (2006.01) | |
| A61K 9/00 | (2006.01) | |
| A61K 9/06 | (2006.01) | |
| A61K 47/34 | (2017.01) | |
| A61K 9/08 | (2006.01) | |
| A61K 47/36 | (2006.01) | |

(52) U.S. Cl.
CPC .......... *A61K 31/722* (2013.01); *A61K 9/0019* (2013.01); *A61K 9/06* (2013.01); *A61K 9/08* (2013.01); *A61K 31/728* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 4,946,870 A * | 8/1990 | Partain, III | A61K 8/736 261/DIG. 88 |
| 2012/0052012 A1 * | 3/2012 | Chenite | A61K 35/14 424/9.1 |
| 2014/0048060 A1 * | 2/2014 | Hiltunen | D01F 2/02 127/33 |

OTHER PUBLICATIONS

Muzzarelli et al (N-(carboxymethylidene)chitosans and N-(carboxymethyl)chitosans: Novel chelating polyampholytes obtained from chitosan glyoxylate. Carbohydrate Research. vol. 107, Issue 2, Sep. 16, 1982, pp. 199-214) (Year: 1982).*

Muzzarelli et al. "Solubility and structure of N-carboxymethylchitosan", Int. J. Biol. Macromol., 1994, 16(4), p. 117-180.

Lu, et al., "Novel hyaluronic acid-chitosan nanoparticles as non-viral gene delivery vectors targeting osteoarthritis", Int. J. Pharm., 2011, 420, p. 358-365.

* cited by examiner

*Primary Examiner* — Jake M Vu
(74) *Attorney, Agent, or Firm* — Norton Rose Fulbright

(57) ABSTRACT

The present disclosure relates to a method which allows direct formation of gel-like solutions of polyglucosamine at neutral pH≈7 to 8, eliminating the need of prior dissolution of polyglucosamine in acidic environment; and to a homogeneous liquid combination of polyglucosamine-glyoxylate with hyaluronan.

11 Claims, 4 Drawing Sheets

Polyglucosamine-glyoxylate in solution

Hyaluronate in solution

X = molecule screen

Coexistence of HA and Polyglucosamine-glyoxylate in solution

Polyglucosamine in solution

Hyaluronate in solution

Ionique bonds

Precipitation of HA-Polyglucosamine complex

COMPOSITION COMPRISING POLYGLUCOSAMINE-GLYOXYLATE SOLUTIONS MIXED WITH HYALURONAN

CROSS-REFERENCE TO RELATED APPLICATIONS

The present application is a continuation of U.S. application Ser. No. 15/008,620 filed Jan. 28, 2016, which is U.S. National Phase of International Application No. PCT/CA2014/050713, filed on Jul. 29, 2014, and claiming priority from U.S. Provisional Application No. 61/859,921 filed Jul. 30, 2013, the content of which is hereby incorporated by reference in its entirety

TECHNICAL FIELD

The present description relates to a composition comprising polyglucosamine-glyoxylate solutions mixed with hyaluronan.

BACKGROUND ART

Polyglucosamine polymers are linear amino-polysaccharides composed of D-glucosamine and N-acetyl-D-glucosamine units linked by (1-4) glycosidic bonds. They are produced by alkaline deacetylation of chitin, a component of the exoskeleton of crustaceans, the cuticles of insects and the cell walls of fungi (Muzzarelli et al., 1986, Chitin in Nature and Technology, Plenium Press, New York). Polyglucosamine contains free amine (—$NH_2$) groups and may be characterized by the proportion of N-acetyl-D-glucosamine units and D-glucosamine units, which is expressed as the degree of deacetylation (DDA) of the fully acetylated polymer chitin. The properties of polyglucosamine, such as the solubility and the viscosity, depend on the degree of deacetylation (DDA), which represents the percentage of glucosamine monomers, and the molecular weight (Mw).

Polyglucosamine polymers have been proposed in various formulations, alone and with other components, to stimulate repair of dermal, corneal and hard tissues (see for example U.S. Pat. Nos. 4,572,906; 4,956,350; 5,894,070; 5,902,798; and 6,124,273; and WO 98/22114). Biodegradability, adhesiveness, and prevention of dehydration as well as the ability to form barrier to bacterial invasion are the properties of polyglucosamine that are most commonly cited as beneficial for the wound healing. The interesting hemostatic potential of polyglucosamine has also been behind their application to stop bleeding at grafts and wound sites (U.S. Pat. No. 4,532,134). Some studies claim that the hemostatic activity of polyglucosamine derives solely from their ability to agglutinate red blood cells while others believe that the polycationic amine character can activate platelets to release thrombin and initiate the classical coagulation cascade. It has been proposed in U.S. Pat. No. 5,773,033 the use of polyglucosamine as a hemostatic agent in combination with fibrinogen and purified autologous platelets.

The non-solubility of polyglucosamine polymers at physiological pH constitutes the main technical difficulty limiting their use in a solution state. Thus typically, dissolution of polyglugosamine is achieved via the protonation of amine groups in acidic aqueous solutions. The resulting solutions have a pH ranging from 3.0 to 5.5 and if neutralized, the polymer remains soluble up to a pH near 6.2. Beyond this pH value, further deprotonation of the amino-groups reduces inter-chain electrostatic repulsion and allows attractive forces of hydrogen bonding, hydrophobic and van der Waals interactions to cause polymer precipitation. The dissolution of polyglucosamine can be carried out using solution of mineral acids, such HCl or organic acids, such as acetic acid.

However, it seems that under particular conditions, the neutralization of polyglucosamine solution up to physiological pH around 7 can be achieved without inducing precipitation. U.S. Pat. No. 6,344,488 discloses a pH-dependent temperature controlled polyglucosamine composition prepared by neutralizing, up to pH between 6.8 and 7.2, with mono-phosphate dibasic salts of polyols or sugars, such as sodium β-glycerophosphate. U.S. patent applications nos. 2009/0270514 and 2010/0113618 described the preparation of thermogelling polyglucosamine solutions by using, either a $(NH_4)_2HPO_4$ solution or a NaOH solution. And more recently, U.S. patent application no. 2012/0052012 teach the preparation of thermogelling solution of polyglucosamine, neutralized to around 7, by glucosamine carbonate and glucosamine phosphate.

Muzzarelli et al. (1982, Carbohydrate Research, 107: 199-214; U.S. Pat. No. 4,835,265) describes the use of oxoacids, such as glyoxylic acid to modify chitosan and produce N-carboxymethyl grafted chitosan. The carboxymethyl group is permanently grafted onto the chitosan chain. The method consists of adding glyoxylic acid to aqueous suspensions of chitosan to cause dissolution of chitosan and gel formation at pH between 4.5 and 5.5. Then alkaline NaOH solution is added to evidence the formation of a Schiff base, namely N-(carboxymethylidene)-chitosan, which is reduced by sodium cyanoborohydride at room temperature to give N-carboxymethyl chitosan.

There is no report or publication teaching the preparation of gel-like solutions of polyglucosamine, just by dispersing polyglucosamine powder into a solution directly at a pH between 7 and 8.

There is still a need to be provided with a method of preparing a gel-like solution of polyglucosamine at neutral pH, without the need of prior dissolution of polyglucosamine in an acidic environment, allowing the resulting dissolved polyglucosamine to be mixed with negatively charged polyelectrolytes to form homogenous liquid mixtures, without inducing precipitation.

SUMMARY

In accordance with the present description there is now provided a method of preparing a composition of polyglucosamine, comprising the step of dissolving the polyglucosamine in a solution of glyoxylate at a pH between of 7 and 8.

In accordance with the present description there is also provided a composition comprising a polyglucosamine, glyoxylate and hyaluronan.

In an embodiment, the polyglucosamine is at least one of chitin, chitosan, polyglucosaminoglycans, chondroitin, heparin, keratan and dermatan.

In another embodiment, the polyglucosamine is chitosan.

In an additional embodiment, the concentration of chitosan ranges from 0.1% to 5.0%; from 1.0% to about 3.0%.

In an embodiment, the chitosan has a degree of deacetylation (DDA) ranging between 70% and 100% and a molecular weight (Mw) ranging from 50 kDa to 1000 kDa.

In a further embodiment, the chitosan has a DDA of 80% to 99%, and a Mw of 200 kDa to 500 kDa.

In a further embodiment, the method described herein further comprises the step of mixing the composition with a negatively charged polyelectrolyte.

In an embodiment, the negatively charged polyelectrolyte is hyaluronan (HA) or alginate.

In another embodiment, the negatively charged polyelectrolyte is hyaluronan (HA).

In an embodiment, the composition described herein further comprises at least one material or compound selected from the group consisting of cells, stem cells, peptides, growth factors, human blood, platelet-rich plasma, nucleotides, bone, bone-derived materials, calcium phosphates, calcium carbonates, bioglasses, ceramics, drugs, cytolines, osteogenic agents, osteoinductive agents and imaging agents.

In another embodiment, the composition is for treating a tissue or organ within a mammalian or human body.

In another embodiment, the mammalian encompassed can be an animal, such as a horse, a dog or a cat.

In a particular embodiment, the tissue or organ comprises articular cartilage, fibrocartilage, meniscus, intervertebral discs, bone tissues, muscular tissues, nerve and spinal cord soft-tissues, skin or dermal tissues.

In a further embodiment, the composition is for treating body joint functions or cartilage defects.

In another embodiment, the composition is formulated for treating inflammatory joint conditions.

In an embodiment, the composition is formulated to be injected into the patient.

In a further embodiment, the inflammatory joint conditions are caused by arthritis.

It is also provided the use of the composition described herein for treating inflammatory joint conditions, osteoarthritis, vitreous humor of the eye, cataract, or corneal grafts.

It is also provided the use of the composition described herein fin the manufacture of a medicament for treating inflammatory joint conditions, osteoarthritis, vitreous humor of the eye, cataract, or corneal grafts.

It is also provided the use of the composition described herein in the manufacture of a viscoelastic ophthalmic composition for cataract surgery.

It is also provided the use of the composition described herein in the manufacture of a cosmetics, ophthalmology, therapeutics delivery, wound healing or tissue engineering composition.

It is also provided the use of the composition described herein for treating a tissue or organ within a mammalian or human body.

It is also provided the use of the composition described herein in the manufacture of a medicament for treating a tissue or organ within a mammalian or human body.

It is also provided the use of the composition described herein for treating body joint functions or cartilage defects.

It is also provided the use of the composition described herein in the manufacture of a medicament for treating body joint functions or cartilage defects.

DETAILED DESCRIPTION

It is provided a method and composition which allows direct formation of gel-like solutions of polyglucosamine at neutral pH$\approx$7 to 8, eliminating the need of prior dissolution of polyglucosamine in acidic environment.

The present description is based on the finding that the specific interaction of polyglucosamine polymers with a glyoxylate aqueous solution (at pH$\approx$7 to 8), allows direct formation of neutral gel-like solutions, eliminating the need of prior acidification and subsequently neutralization. The gel-like solutions described here have the ability to form clear and homogeneous liquid mixtures, free from any precipitation, with a negatively charged polyelectrolyte such as a hyaluronate (HA) solution.

Figure 1:
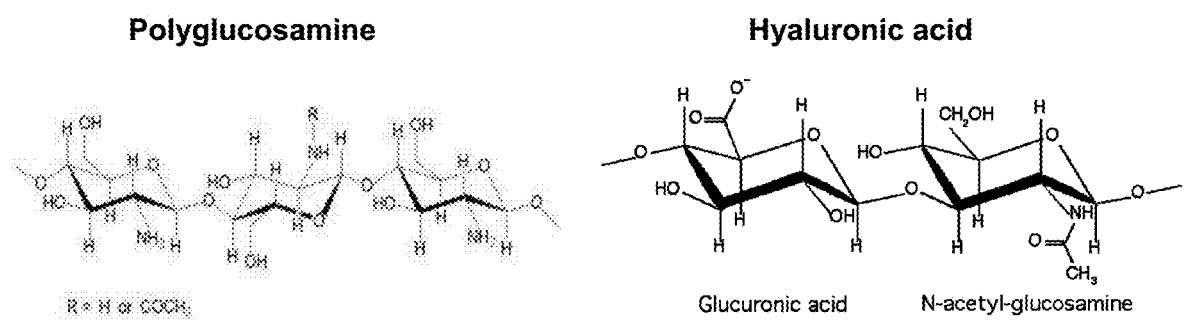
FIG. 1 shows the structures of polyglucosamine and hyaluronic acid.

Polyglucosamine polymers are linear amino-polysaccharides composed of D-glucosamine and N-acetyl-D-glucosamine units linked by (1-4) glycosidic bonds (see FIG. 1). Polyglucosamine contains free amine (—$NH_2$) groups and may be characterized by the proportion of N-acetyl-D-glucosamine units and D-glucosamine units, which is expressed as the degree of deacetylation (DDA) of the fully acetylated polymer chitin. The non-solubility of polyglucosamine polymers at physiological pH constitutes the main technical difficulty limiting their use in a solution state. Thus typically, dissolution of polyglugosamine is achieved via the protonation of amine groups in acidic aqueous solutions. The resulting solutions have a pH ranging from 3.0 to 5.5 and if neutralized, the polymer remains soluble up to a pH near 6.2. Beyond this pH value, further deprotonation of the amino-groups reduces inter-chain electrostatic repulsion and allows attractive forces of hydrogen bonding, hydrophobic and van der Waals interactions to cause polymer precipitation.

Glyoxylate is the conjugate base of glyoxylic acid, an environmentally and toxicologically safe biochemical. It is generally highly versatile for chemical synthesis and is therefore produced in high market volumes. Glyoxylate is an intermediary in glyoxylate cycle, which allows microorganisms, such as bacteria, fungi and plants to convert fatty acids into carbohydrates. Glyoxylate is also a by-product in the biosynthesis of amide peptides.

Figure 2:
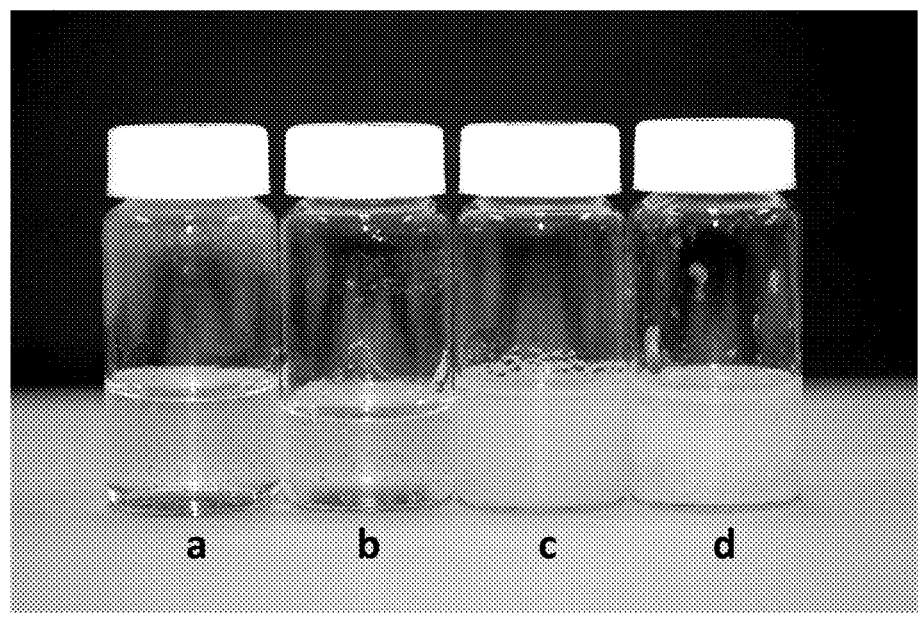
FIG. 2 shows the viscous and clear and homogeneous solution obtained upon mixing polyglucosamine-glyoxylate with hyaluronic acid sodium salt (HA).

The composition described herein consists on the dispersion of polyglucosamine into a glyoxylate aqueous solution (at pH$\approx$7-8), where specific interaction between polyglucosamine's amino groups and glyoxylate anions allows the formation of neutral gel-like solution (see FIG. 2a). Indeed, the amino groups of polyglucosamine react with the aldehyde function of glyoxylate to form imine bond and water. This reversible reaction is schematised as follow.

$$\text{Polyglucosamine-}NH_2 + \underset{\text{Glyoxylate}}{\overset{O}{\underset{H}{\vphantom{O}}}\!\!C\!-\!\overset{O}{\underset{O^-Na^+}{\vphantom{O}}}\!\!C} \rightleftharpoons \underset{\text{Imine formation}}{-N\!=\!C\!-\!\overset{O}{\underset{O^-Na^+}{\vphantom{O}}}\!\!C} + H_2O$$

In one aspect, the present application proposes to take benefit from the reversibility of imine bond to design injectable polyglucosamine-glyoxylate gel-like solutions. When such solutions are injected in vivo, the reverse reaction allows the progressive deposition of original polyglucosamine at the injection site.

Figure 3:
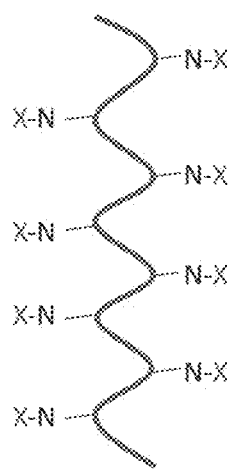
FIG. 3 is a schematic illustration showing the coexistence of polyglucosamine-glyoxylate and HA dissolved in the mixture solution.
Figure 3:
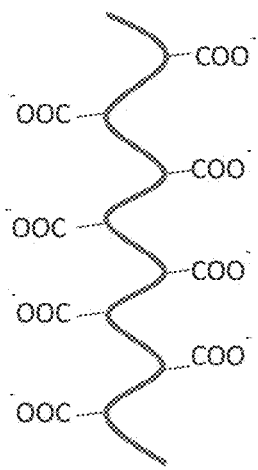
Figure 3:
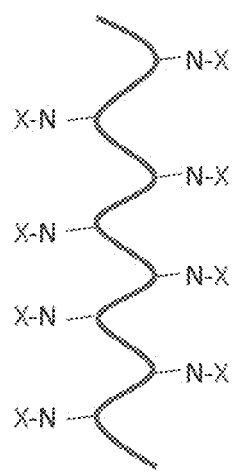
Figure 3:
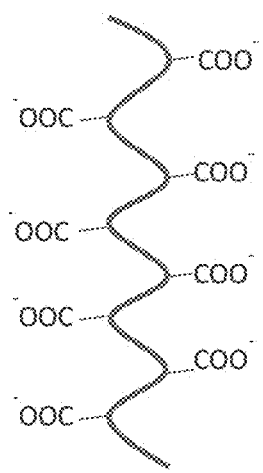
Figure 5:
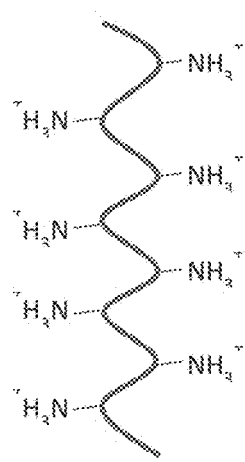
FIG. 5 is a schematic illustration showing the formation of complex precipitate upon the mixing of polyglucosamine solution with HA solution.
Figure 5:
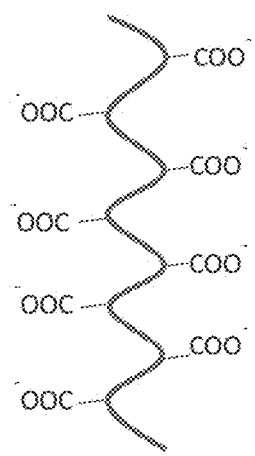
Figure 5:
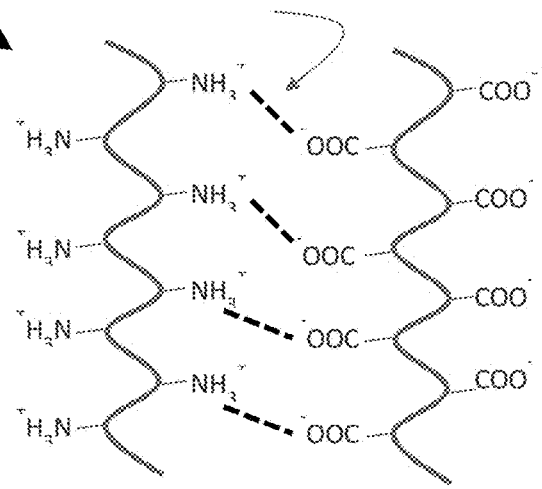

In another aspect, the resulting neutral polyglucosamine-glyoxylate solutions have the particularity to be mixed with solutions of negatively charged polyelectrolyte, such as hyaluronate and alginate solutions, to form homogeneous and clear liquid mixtures, free from any precipitate (see FIGS. 2b and 3). The absence of precipitation is due to the very low content of charged amino groups. As seen in FIG. 5, ionic bonds are formed for example when sodium glyoxalate has been replaced either by glyoxylic acid or by hydrochloride acid, causing precipitation (see FIGS. 2c and d). I In polyglucosamine-glyoxylate solutions where the pH is between 7 and 8, less than 17% of un-reacted amino groups can be positively charged or protonated. In addition, it can be estimated that more than 50% of amines should be imine-linked to glyoxylate in order to form polyglucosamine gel-like solutions. In contrast, for polyglucosamines dissolved in acids, the pH is usually between 4.5 and 5.5. At this level of pH, more than 90% of amino groups are protonated, and then if such solutions are mixed to anionic polyelectrolyte solutions, such as HA or alginate solutions, polyelectrolyte complexes are instantaneously formed.

Typical polyglucosamines include, for example, chitin, chitosan, and polyglucosaminoglycans which are copolymers of N-acetylglucosamine and various glycan sugars, e.g. chondroitin, heparin, keratan and dermatan.

Particularly, chitosan is an amino polysaccharide obtained by partial to substantial alkaline N-deacetylation of chitin also named poly(N-acetyl-D-glucosamine), which is a naturally occurring biopolymer found in exoskeleton of crustaceans, such as shrimp, crab and lobster shells. Chitosan contains free amine (—$NH_2$) groups and may be characterized by the proportion of N-acetyl-D-glucosamine units and D-glucosamine units.

Chitosan is thus recognized as a biodegradable, biocompatible, antibacterial and hemostatic biopolymer that is able to promote wound healing, drug absorption, and tissue reconstruction. Chitosan also has been widely explored in numerous cosmetic and pharmaceutical applications. Therefore, considering the great potential of chitosan, there is a continuous need to improve the properties of known thermosensitive chitosan hydrogels which are still considered as very promising for a wider range of biomedical applications.

In vivo, chitosan compositions and materials have been tested in various animal models and through several administration routes. Chitosan has been safely studied in mouse models (immunogenicity), rat models, guinea pig models, and rabbit models (sub acute toxicity). No "significant toxic effects" of chitosan were noted in acute toxicity tests in mice, no eye or skin irritation in rabbits and guinea pigs respectively. In the same study it was also concluded that chitosan was not pyrogenic. Exposure of rat nasal mucosa to chitosan solutions at 0.5% (w/v) over 1 h caused no significant changes in mucosal cell morphology compared to control. From most studies reported it appears that chitosan shows minimal toxic effects and this justifies its selection as a safe material in drug delivery. Chitosan β-glycerophosphate systems have been investigated in vitro, in vivo in animal models and in humans, and have shown a safe and non-toxic profile (Hirano et al., 1991, Agric. Biol. Chem., 55: 2623-2625; Ono et al., 2000, J. Biomed. Mater. Res., 49: 289-295; Azad et al., 2004, J. Biomed. Mater. Res. B Appl. Biomater., 69: 216-222; Ishihara et al., 2001, Wound Repair Regen., 9: 513-52; and Ilium et al., 1994, Pharm. Res., 11: 1186-1189).

In humans, a phase two clinical trial involving the percutaneous injection of chitosan-[166]holmium complex, for the treatment of hepatocellular carcinoma, on patients with poor surgical prospects, reported safe and efficacious results. The effects of chitosan have been investigated on eighty patients with renal failure undergoing long-term stable haemodialysis treatment. The patients were tested after a control treatment period of 1 week. Half were fed 30 chitosan tablets (45 mg chitosan/tablet) three times a day. Ingestion of chitosan effectively reduced total serum cholesterol levels (from 10.14+/−4.40 to 5.82+/−2.19 mM) and increased serum haemoglobin levels (from 58.2+/−12.1 to 68+/−9.0 g L−1). During the treatment period, no clinically problematic symptoms were observed. The results suggest that chitosan might be an effective treatment for renal failure patients, although the mechanism of the effect should be investigated further.

Chitosan was also administrated intranasal to deliver morphine in patients following orthopedic surgery, and was shown to offer a safe and less invasive alternative to intra venous (IV) morphine. An clinical and pharmacokinetic study for a drug delivery system (DDS) of gentamycin-loaded chitosan bar were carried out with the purpose to evaluate its efficacy and giving further data for its clinical applications. Eighteen cases of chronic osteomyelitis were treated by surgical necrectomy with implantation of gentamycin-load chitosan bar in the prepared bone cavity. All of the eighteen cases were followed up for 24.8 months (in a range of 6-34 months) sixteen patients received initial cure and without any recurrence. So, it could be concluded that the gentamycin-loaded chitosan DDS was a simple and effective method for the treatment of chronic osteomyelitis without the necessity to carry out a second operation to remove the drug carrier.

In China, on twelve patients, chitosan was observed to safely prevent or reduce elbow adhesion after elbow arthrolysis. It was investigated again in humans to prevent knee adhesion following patella operation (Kim et al., 2006, Clin. Cancer Res., 12: 543-548; Jing et al., 1997, J Pharm Pharmacol., 49(7): 721-723; Stoker et al., 2008, Pain Med., 9: 3-12; and Chen et al., 1998, Chinese Journal of Reparative and Reconstructive Surgery, 12: 355-358).

Several clinical trials involving chitosan compositions or materials for drug delivery or medical implant purposes are ongoing (recruiting) or terminated in the United States. Chitosan materials are, or have been, clinically studied in patients for the management of difficult spontaneous epistaxis and to evaluate its healing effect on nasal mucosa, to investigate the safety and efficacy of hemostasis of the dressing for use in dental surgical procedures, to test a chitosan pad after diagnostic percutaneous coronary angiography as an adjunct to manual compression to better control vascular access site bleeding and reduce time-to-hemostasis, to investigate a chitosan composition as a safe, effective debridement of chronic wounds in the operating room and inpatient ward settings and to minimize bacterial re-colonization of wounds, to investigate the therapeutic benefits of using a chitosan composition for the wound repair of diabetic neuropathic foot ulcers, to compare the efficacy of a chitosan composition versus conventional treatment in the treatment of Diabetic Neuropathic Foot Ulcer, to investigate a new chitosan derivative for reducing the symptoms associated with Dry Eye Syndroma, and to investigate whether the treatment of damaged cartilage in the knee with a chitosan composition will increase the amount and quality of cartilage repair tissue when compared with microfracture alone. Moreover, chitosan materials are, or have been, clinically studied in patients to determine if chitosan, a short-chained chitosan with a molecular weight of 40 kDa, is safe and effective in lowering LDL-cholesterol levels in patients with mild to moderately elevated cholesterol levels (drug), and to compare safety and immunogenicity of two dosage levels of Norwalk VLP Vaccine with chitosan adjuvant/excipients.

Hyaluronan (also called hyaluronic acid or hyaluronate or HA) is a naturally occurring linear polysaccharide belonging to the class of non-sulfated glycosaminoglycans (see FIG. 1). Its repeating unit is a disaccharide composed of β-1,4-N-acetyl-D-glucosamine and β-1,3-D-glucuronic acid. HA is found in cartilage, synovial fluid and skin tissue. HA is used in a variety of applications including osteoarthritis, cosmetics, ophthalmology, therapeutics delivery, wound healing and tissue engineering. Because HA is water-soluble and is degraded and eliminated rapidly in vivo, the potential application for HA in biomedical purposes have been somewhat limited.

HA is known to perform a number of functions in man and other animals including the lubrication of the joints, the maintenance of the gel-like character of the vitreous humor of the eye and the contribution to the ground substance around cells where it functions as an inter-cellular lubricant and flexible cement. HA is well accepted by the ophthalmic community as a compound that can protect biological tissues or cells from compressive forces. Accordingly, HA has been proposed as a component of a viscoelastic ophthalmic composition for cataract surgery. HA has been used to maintain the hydration and condition of the eye during various surgical procedures such as corneal grafts. More recently, because of its joint lubricant function, investigations have been directed in an attempt to use HA to alleviate the inflammatory joint conditions such as arthritis. In animals such as the horse, it is currently used as a method of treatment of inflammatory joint conditions.

In addition, because it is known to be a constituent of the ground substance of cells, HA is being incorporated into various cosmetic preparations for the skin. In this role it is proposed that the addition of HA to the skin is able to raise the level of HA present in the cells coats in the dermal layers thereby improving the condition of the skin. HA is also applied to the skin for healing wounds, burns, skin ulcers, and as a moisturizer. There is also a lot of interest in using hyaluronic acid to prevent the effects of aging.

It is provided a homogeneous liquid combination of polyglucosamine-glyoxylate with HA which can be used for example in order to significantly increase the residence time of the later in vivo. Indeed, when such combination is injected in vivo, the glyoxylate species are released from polyglucosamine-glyoxylate through the reverse reaction, and thus the cationic charge density of polyglucosamine is increased (see FIG. 3). This results into stronger attractions with HA, thus preventing its rapid elimination and enhancing its retention time.

The present disclosure will be more readily understood by referring to the following examples which are given to illustrate embodiments rather than to limit its scope.

Example I

Preparation of a Mixture of
Polyglucosamine-Glyoxylate and Hyaluronate

The following examples describe the preparation of homogeneous and clear mixture of polyglucosamine with hyaluronate (HA) in presence of sodium glyoxylate.

A suspension of 0.1110 g of polyglucosamine (80%) in 5 mL of water is added with 0.0739 g of sodium glyoxylate. A gel-like solution is formed within 1 hour at a physiological pH.

Afterwards, 5 mL aqueous solution (2%) of hyaluronic acid sodium salt (HA) was added and thoroughly mixed with the gel-like solution of polyglucosamine/glyoxylate. The resulting mixture is viscous and clear homogeneous solution free from any precipitate as can be seen in FIG. 2a.

Figure 4:
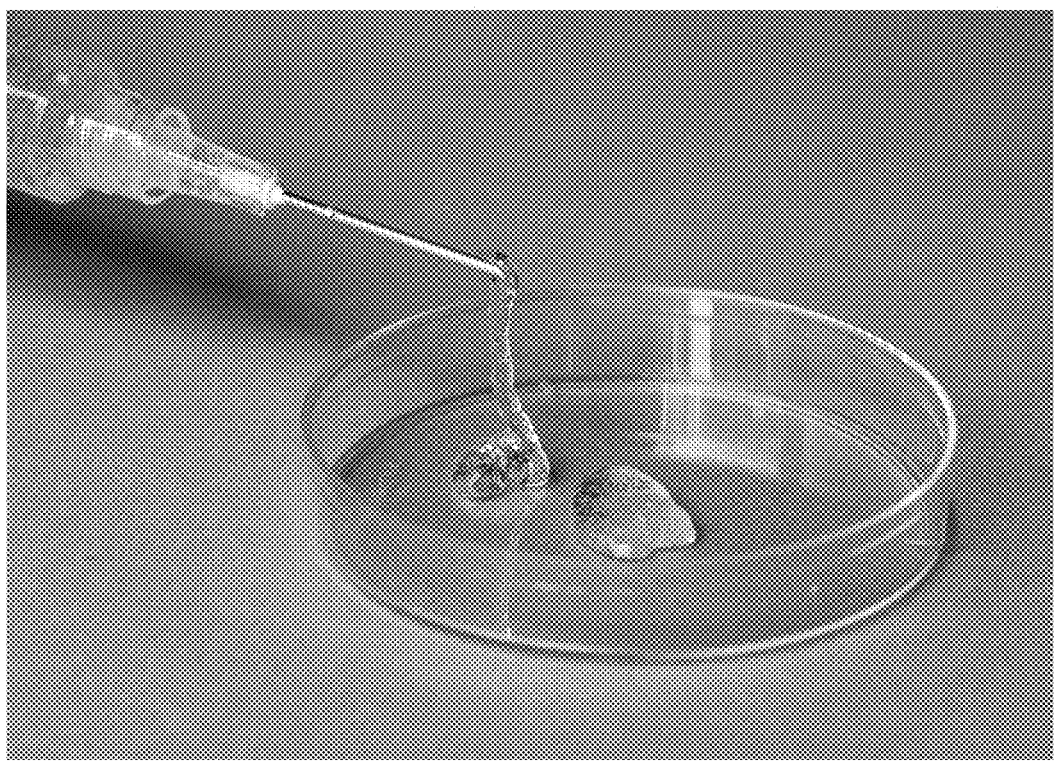
FIG. 4 shows the ease injectability of the mixture of polyglucosamine-glyoxylate and HA.

Further, a mass of 0.2007 g of HA is added to a suspension of 0.1091 g of polyglucosamine (80%) in 10 mL of water, under stirring. The stirring is continued until complete dissolution of HA, which results in viscous solution where polyglucosamine particles are homogeneously dispersed. Then, 0.0720 g of sodium glyoxylate is added while maintaining stirring for about 3 to 4 hours until entire solubilisation of polyglucosamine. The resulting mixture consists of clear and homogeneous viscous solution as shown in FIG. 2b. The pH of the mixture is in the physiological range, between 7 and 8. Both mixtures prepared can be easily injectable as shown in FIG. 4.

Example II

Preparation of a Mixture of
Polyglucosamine-Glyoxylic Acid with HA

A volume of 10 mL of water is added to 0.1088 g of polyglucosamine powder under stirring to create a homogeneous dispersion, to which a mass of 0.2017 g of HA is then added. The stirring is maintained for about 2 to 3 hours until complete dissolution of HA and viscous dispersion is obtained. Then, 0.72 mL of glyoxylic acid solution (1M) is added and the stirring continued. The resulting mixture turned into white due to the presence of white hydrated precipitate, as shown in FIG. 2c, indicating an instantaneous formation of a complex between polyglucosamine and HA. Such result can be expected by any skilled person in the art because polyglucosamine and HA are two polyelectrolytes of opposite charges.

Example III

Preparation of a Mixture of Polyglucosamine-HCl
with HA

A mass of 0.1092 g of polyglucosamine is dissolved in 5 mL of HCl solution (77 mM) and then mixed with 5 mL of HA aqueous solution (2%). The mixture turned instantaneously to a white hydrated precipitate indicating the formation of a complex between positively polyglucosamine and negatively charged Hyaluronate (HA). With time the precipitate clearly separate from the solution as can be seen in FIG. 2d.

While the description has been described in connection with specific embodiments thereof, it will be understood that it is capable of further modifications and this application is intended to cover any variations, uses, or adaptations of the disclosure, including such departures from the present disclosure as come within known or customary practice within the art to which the disclosure pertains and as may be applied to the essential features hereinbefore set forth, and as follows in the scope of the appended claims.

What is claimed is:

1. A method of preparing a composition of polyglucosamine and a negatively charged polyelectrolyte, comprising the steps of:

a) dissolving the polyglucosamine in a solution of glyoxylate at a pH between of 7 and 8, wherein amino groups of the polyglucosamine react with aldehyde functions of the glyoxylate to form imine bond and water forming a neutral gel-like solution of dissolved polyglucosamine; and b) mixing the neutral gel-like solution of dissolved polyglucosamine with the negatively charged polyelectrolyte, wherein no heating is used to dissolve the polyglucosamine.

2. The method of claim 1, wherein the negatively charged polyelectrolyte is hyaluronan (HA) or alginate.

3. The method of claim 1, wherein the negatively charged polyelectrolyte is hyaluronan (HA).

4. The method of claim 1, wherein the polyglucosamine is at least one of chitin, chitosan, polyglucosaminoglycans, chondroitin, heparin, keratan and dermatan.

5. The method of claim 1, wherein the polyglucosamine is chitosan.

6. The method of claim 5, wherein the concentration of chitosan ranges from 0.1% to 5.0%.

7. The method of claim 5, wherein the concentration of chitosan ranges from 1.0% to about 3.0%.

8. The method of claim 5, wherein said chitosan has a degree of deacetylation (DDA) ranging between 70% and 100% and a molecular weight (Mw) ranging from 50 kDa to 1000 kDa.

9. The method of claim 5, wherein said chitosan has a DDA of 80% to 99%, and a Mw of 200 kDa to 500 kDa.

10. The method of claim 1, further comprising adding to the composition at least one material or compound selected from the group consisting of cells, stem cells, peptides, growth factors, human blood, platelet-rich plasma, nucleotides, bone, bone-derived materials, calcium phosphates, calcium carbonates, bioglasses, ceramics, drugs, cytolines, osteogenic agents, osteoinductive agents and imaging agents.

11. The method of claim 1, wherein the composition comprises chitosan dispersed in a glyoxylate solution, glucosamine carbonate or glucosamine phosphate, and hyaluronan.

* * * * *